(12) United States Patent
Corradi et al.

(10) Patent No.: US 8,877,014 B2
(45) Date of Patent: Nov. 4, 2014

(54) SPLIT-SHELL FRACTIONATION COLUMNS AND ASSOCIATED PROCESSES FOR SEPARATING AROMATIC HYDROCARBONS

(71) Applicant: UOP LLC, Des Plaines, IL (US)

(72) Inventors: Jason T. Corradi, Arlington Heights, IL (US); David William Ablin, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/715,774

(22) Filed: Dec. 14, 2012

(65) Prior Publication Data

US 2014/0171715 A1  Jun. 19, 2014

(51) Int. Cl.
*B01D 3/04* (2006.01)
*C10G 1/04* (2006.01)
*B01D 3/32* (2006.01)
*B01D 3/14* (2006.01)

(52) U.S. Cl.
CPC . *B01D 3/141* (2013.01); *B01D 3/32* (2013.01)
USPC ............... 196/111; 196/98; 196/125; 208/89; 208/107

(58) Field of Classification Search
USPC ........................ 196/111, 98, 125; 208/89, 107
See application file for complete search history.

(56) References Cited

U.S. PATENT DOCUMENTS

| | | | |
|---|---|---|---|
| 2,695,323 A | 11/1954 | Arnold et al. | |
| 5,720,872 A * | 2/1998 | Gupta | 208/57 |
| 5,912,395 A | 6/1999 | Noe | |
| 6,379,535 B1 * | 4/2002 | Hoehn et al. | 208/107 |
| 6,679,939 B1 * | 1/2004 | Thiel et al. | 95/210 |
| 6,858,128 B1 * | 2/2005 | Hoehn et al. | 208/111.3 |
| 7,622,034 B1 * | 11/2009 | Thakkar et al. | 208/210 |
| 8,518,240 B2 * | 8/2013 | Serban et al. | 208/64 |
| 8,574,425 B2 * | 11/2013 | Hoehn et al. | 208/82 |
| 2011/0259793 A1 * | 10/2011 | Umansky et al. | 208/89 |

FOREIGN PATENT DOCUMENTS

DE  203471 A1  10/1983

OTHER PUBLICATIONS

New Exchanger Design Keeps Puerto Rico BTX Plant Operating,Oil & Gas Journal (ISSN 0030-1388) V96 N. 43 88-89 (Oct. 26, 1998), v 96, n. 43, p. 88-89, Oct. 26, 1998; ISSN: 00301388; Publisher: PennWell.

* cited by examiner

*Primary Examiner* — Nina Bhat
(74) *Attorney, Agent, or Firm* — Maryann Maas

(57) ABSTRACT

Split-shell fractionation columns and associated processes for separating aromatic hydrocarbons. A split-shell fractionation column includes a housing shell having a first height and a partition having a second height and disposed within the housing shell. The partition includes first and second vertically oriented baffles separated by a gap region, a seal plate connecting top ends of the baffles, a first input port formed to extend through the partition for the introduction of a gas into the gap region, and a first output port formed to extend outwardly from a bottom of the gap region and through the housing shell. The partition defines a first distillation zone and a second distillation zone within the housing shell.

16 Claims, 2 Drawing Sheets

SPLIT-SHELL FRACTIONATION COLUMNS AND ASSOCIATED PROCESSES FOR SEPARATING AROMATIC HYDROCARBONS

TECHNICAL FIELD

The technical field relates generally to chemical separation processes and associated apparatus. More particularly, the disclosure relates to processes for the separation of an aromatic hydrocarbon isomer, for example a xylene isomer, from a feed stream containing a mix of aromatic and non-aromatic hydrocarbons using a split-shell fractionation column.

BACKGROUND

Aromatic hydrocarbons find a plurality of uses in various chemical synthesis industries. In one non-limiting example, para-xylene is an important intermediate aromatic that finds wide and varied application in chemical syntheses. Upon oxidation, para-xylene yields terephthalic acid. Polyester fabrics and resins are produced from a polymer of ethylene glycol and terephthalic acid. These polyester materials are used extensively in a number of industries and are used to manufacture such items as, for example, clothing, beverage containers, electronic components, and insulating materials.

In prior art processes, $C_9$ aromatic hydrocarbons are separated from $C_8$ aromatic hydrocarbons, for example xylene isomers, by fractional distillation. This requires heating of the admixture to vaporize the $C_8$ and lighter aromatic hydrocarbons. A large portion of the isomerization stream must be vaporized to accomplish the $C_9$ separation because the stream is generally composed primarily of $C_8$ and lighter aromatic hydrocarbons. After the $C_9$ aromatic removal, the $C_8$-containing stream is then recycled into an adsorptive separation unit. Multiple, large fractionation columns are often required to accomplish these process steps. As such, this separation process requires a substantial amount of energy and associated capital costs.

The production of aromatic hydrocarbon isomers, including for example para-xylene, is practiced commercially in large-scale facilities and is highly competitive. A never-ending drive exists to decrease the energy costs and capital costs yet increase the effectiveness associated with the conversion of a feedstock through one or more of isomerization, transalkylation, and disproportionation to produce select isomers and separate the select isomers from the resultant mixture of $C_8$ aromatic isomers.

Accordingly, it is desirable to provide processes for the production of particular aromatic isomers, including the separation of such isomers from an admixture of $C_8$ and $C_9$ aromatic isomers, that lowers operational expenses, particularly energy consumption. In addition it is desirable to provide processes for the production of particular aromatic isomers that lowers capital expenditures, in the form of processing equipment and the size of such processing equipment. Further, it is desirable to provide split-shell fractionation columns for use in such processes. These and other desirable features and characteristics will become apparent from the subsequent detailed description and the appended claims, taken in conjunction with the accompanying drawings and the foregoing technical field and background.

BRIEF SUMMARY

Split-shell fractionation columns and associated processes for separating aromatic hydrocarbons are provided herein. In one exemplary embodiment of the present disclosure, a split-shell fractionation column includes a housing shell having a first height and a partition having a second height and disposed within the housing shell. The partition includes first and second vertically oriented baffles separated by a gap region, a seal plate connecting top ends of the baffles, a first input port formed to extend through the partition for the introduction of a gas into the gap region, and a first output port formed to extend outwardly from a bottom of the gap region and through the housing shell. The partition defines a first distillation zone and a second distillation zone within the housing shell.

In another exemplary embodiment of the present disclosure, a process for separating aromatic hydrocarbons includes the steps of introducing a first stream including a plurality of aromatic hydrocarbons into a first distillation zone of a split-shell fractionation column and introducing a second stream including a plurality of aromatic hydrocarbons into a second distillation zone of the split-shell fractionation column. The first and second distillation zones are defined by a partition within the split-shell fractionation column. The partition has a gap region located therein. The process further includes the step of separating the first stream into a first overhead product and a first bottom product. The first bottom product includes a first liquid that collects at a bottom portion of the first distillation zone. The process further includes the step of separating the second stream into a second overhead product and a second bottom product. The second bottom product includes a second liquid that collects at a bottom portion of the second distillation zone. Still further, the process includes the step of draining the first liquid, the second liquid, or a combination thereof in the gap region through a first outlet port.

BRIEF DESCRIPTION OF THE DRAWINGS

The split-shell fractionation column and its associated processes will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Para-xylene, or any other select aromatic hydrocarbon isomer as may be desired, is typically recovered from a mixed aromatic hydrocarbon fraction derived from various sources such as catalytic reforming of petroleum by adsorptive separation, liquid-liquid extraction, and/or fractional distillation. The select aromatic isomer is then separated from that fraction, which typically contains all three xylene isomers, namely ortho-xylene, meta-xylene, and para-xylene. The para-xylene, or other desired isomer, is separated from the fraction to isolate the desired isomer.

Figure 1:
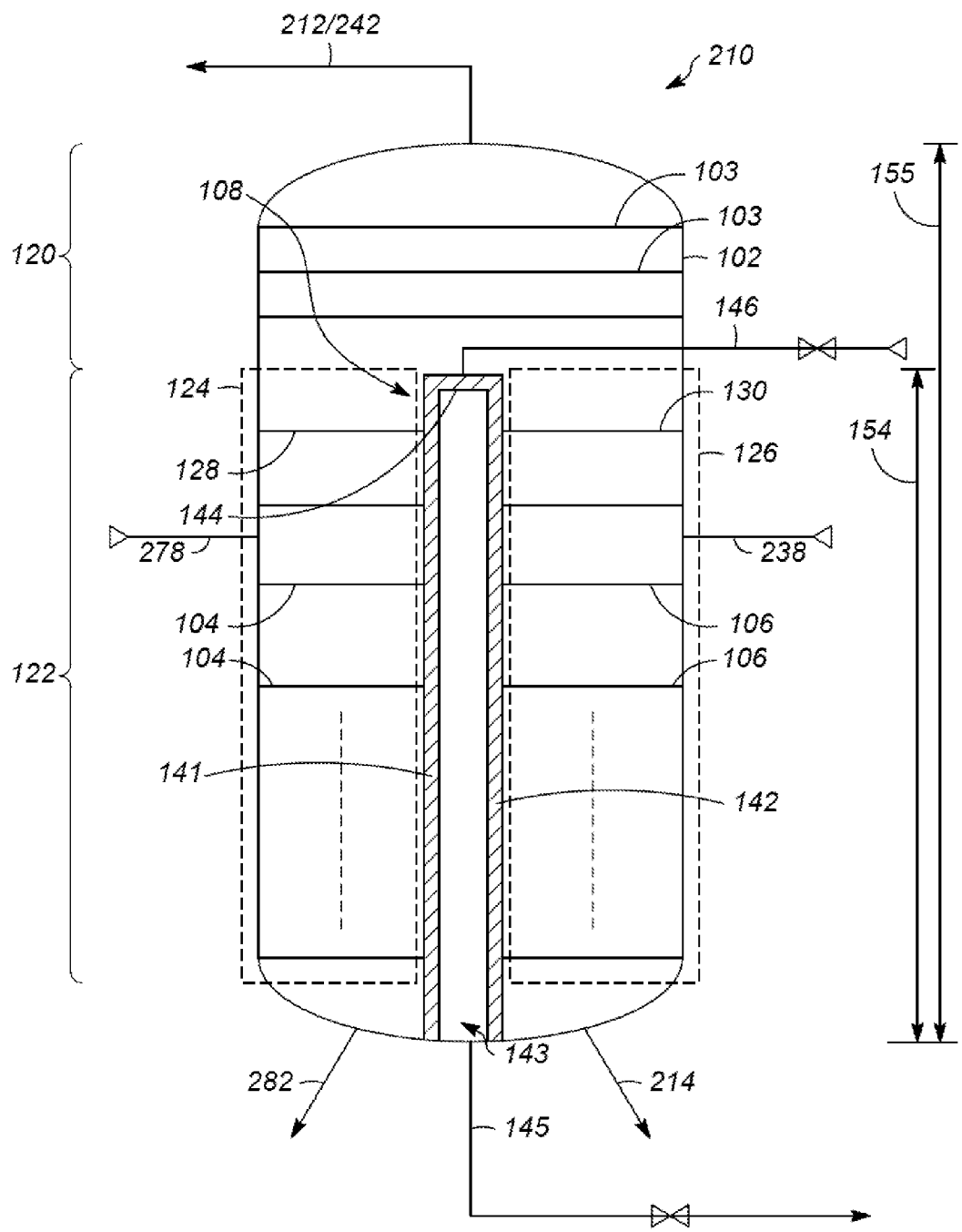
FIG. 1 is a schematic view of an exemplary embodiment of a split-shell fractionation column in accordance with the present disclosure.

FIG. 1 illustrates an exemplary embodiment of a split-shell fractionation column 210. Split-shell fractionation column 210 includes housing shell 102, an upper portion 120, and a lower portion 122. The housing shell 102 has a height 155.

Upper portion 120 includes a plurality of column trays 103. Column trays 103 may be implemented as conventional fractionation column trays as are well-known in the art. Lower portion 122 is divided lengthwise by a partition 108, which extends upwardly from housing shell 102 of bottom portion 122, to create lower distillation zones 124 and 126. The partition has a height 154. Height 154 of the partition 108 is less than height 155 of the housing shell 102. The partition 108 prevents the liquid bottom product, described below, in the lower distillation zones from mixing. Each of the lower distillation zones 124 and 126 have trays 104 and 106, respectively, that are conventional distillation column trays that have been shaped to accommodate the wall of the partition 108 and the housing shell 102. Each of the distillation zones 124 and 126 produce a different liquid bottom product (bottom product streams 214 and 282) from different feed streams fed thereto (input streams 238 and 278) to the fractionation column 210 by virtue of the partition 108 separating the distillation zones 124 and 126. The partition 108 prevents the liquid bottom products in the lower distillation zones from mixing.

A potential problem with some prior art split-shell arrangements is leakage across the partition, in particular in the column "sump" near the bottom of the column where the liquid bottom product inventories are kept separate. Leakage across the partition, which sometimes occurs due to imperfect welding joints or metal fatigue, could contaminate the liquid bottom products, which could erode or eliminate the benefits of the split-shell design. This is particularly important if one of the liquid bottom products is a product for sale instead of an intermediate stream to be recycled for further processing. The presently disclosed split-shell fractionation column 210 addresses this potential leakage.

With continued reference to FIG. 1, input stream 278 is introduced into lower distillation zone 124. Input stream 278, in one embodiment, includes a mixture of $C_8$ aromatic hydrocarbons, $C_9$ and higher aromatic hydrocarbons (hereinafter referred to as $C_9+$ aromatic hydrocarbons), and toluene, for example. Input stream 238 is introduced into the lower distillation zone 126. Input stream 238, in one embodiment, includes a mixture of $C_8$ aromatic hydrocarbons and toluene, for example. In one embodiment, input stream 238 includes a relatively high concentration of para-xylene. That is, in one embodiment, the para-xylene concentration of input stream 238 is higher than the para-xylene concentration of input stream 278. Of course, these compositions are merely non-limiting examples and are provided to illustrate the operation of column 210.

Combining the hydrocarbons from input streams 278 and 238 into a single stream for fractional distillation in a prior art column (i.e., a column without the partition 108) would result in the undesirable dilution of the high purity material in input stream 238. In addition, such combining would introduce undesirable $C_9+$ aromatic hydrocarbons into subsequent processes. The split-shell design allows the two input streams to be distilled separately, while still using only a single distillation column instead of two separate distillation columns, thereby reducing capital expenditures and operational energy costs.

In the operation of the split-shell fractional column 210, the lighter components (i.e., those with a lower boiling point, for example some $C_8$ components and lighter components) introduced to the column 210 via inputs 278 and 238 vaporize at the temperature of the lower portion 122. As such, these lighter components travel upwardly in column 210. In one embodiment, the toluene present ($C_7$) is extracted as a liquid at a side cut tray (not shown) and light hydrocarbons such as $C_6$ and lower hydrocarbons (hereinafter referred to as $C_6—$ hydrocarbons) are extracted as a vapor at an overhead stream 212/242. In another embodiment, the toluene is extracted as a vapor in the overhead stream 212/242 and condensed to form a liquid stream. In one embodiment, the stream 212/242 includes high purity toluene. In another embodiment, the stream 212/242 includes toluene and light hydrocarbons ($C_6—$).

The heavier components (i.e., those with a higher boiling point, for example some $C_8$ components and heavier components) will remain in liquid form and, therefore, will remain in the lower distillation zone 124, if introduced by way of input stream 278, or will remain in lower distillation zone 126, if introduced by way of input stream 238. As such, the heavier fractions of the input stream 278 and input stream 238 will remain segregated in the lower portion 122. In one embodiment, the bottom product stream 282 is a mixture of $C_8$ aromatic hydrocarbons, $C_9+$ aromatic hydrocarbons, and heavier hydrocarbons. In one embodiment, the bottom product stream 214 is a stream including primarily para-xylene. Again, these non-limiting, exemplary stream components are provided merely to illustrate the operation of the split-shell 210 column in one embodiment.

The number of trays 103, 104, and 106 in each of the upper portion 120, lower distillation zone 124, and lower distillation zone 126, respectively, vary with the particular product input streams and desired output streams, as will be appreciated by those skilled in the art. In one embodiment, the number of trays in lower distillation zone 124 is different than the number of trays in lower distillation zone 126, for example the number of trays in distillation zone 124 may be greater than the number of trays in distillation zone 126, or via versa. In an alternative embodiment, the number of trays in lower distillation zone 124 is the same as the number of trays in lower distillation zone 126.

The locations of input streams 278 and 238 on split-shell fractionation column 210 are selected to prevent any mixing of the heavy ($C_8+$) constituents across partition 108. In one embodiment, the partition 108 extends 4 trays above the highest of the feed trays (not shown), trays 128 and 130 being the highest trays in distillation zones 124, 126, respectively. Feed trays, as used herein, refer to the first trays encountered by input streams 238 and 278 upon entry into the column 210. In one embodiment, the partition extends greater than 4 trays above the highest of the feed trays. In one embodiment, the partition extends less than 4 trays above the highest of the feed trays. As used herein, with reference to fractional distillation columns, the term "above" refers to a location in or on the column such that liquid inserted at the location will flow down toward the reference point. Similarly, the term "below" refers to a location in or on the column such that liquid inserted at the location will flow down away from the reference point.

Greater detail is now provided regarding the partition 108 as shown in FIG. 1. The partition 108 is designed so as to mitigate the risk of leakage and cross-contamination of the liquid bottom products. The partition includes two vertical baffles 141, 142 with a gap 143 between these baffles. Any leakage of liquid bottom products through the baffles 141, 142 is collected in a space 143 between the baffles 141, 142, and can be removed by periodic or continuous draining from the column 210 via line 145.

The partition 108 further includes a seal plate 144 at the top of the partition 108 to create a closed system, effectively a "pressure vessel" within the fractionation column 210. The partition space 143, in one embodiment, is operated at a lower pressure than the column 210 such that any and all leakage through either baffle 141, 142 flows from the relatively higher pressure column 210 into the partition space 143. Nitrogen or another suitable inert vapor is used to maintain the pressure inside the partition space 143, and is introduced via line 146. A drain connection is provided to remove liquid accumulation in the bottom of the partition space 143 via line 145.

The exemplary fractionation column 210, and in particular the "pressure vessel" therewithin, is made by welding two vertical baffle plates 141, 142 into the fractionation column 210 with a gap, which in one embodiment can be sized from about 25 mm to about 50 mm, for example from about 30 to about 40 mm, between the two plates 141, 142 to create a partition 108 with space 143 therein. Each plate 141, 142 is welded along the vessel shell so that there is no direct fluid communication between the opposite sides of the baffle plates 141, 142. The top of the baffle plates 141, 142 are welded to the cover plate 144 that effectively closes the gap and prevents fluid communication between the inside of the partition and the fractionation column 210. A vapor inlet connection is made to introduce nitrogen or appropriate inert vapor to maintain an operating pressure within the partition space 143 that is lower than the operating pressure of the column. An outlet connection with an output port is made at the bottom of the partition space 143 to remove any liquid that may accumulate inside the partition space 143 due to unintended leakage through the baffles 141, 142, for example due to an imperfect weld connection.

ILLUSTRATIVE EXAMPLE

Figure 2:
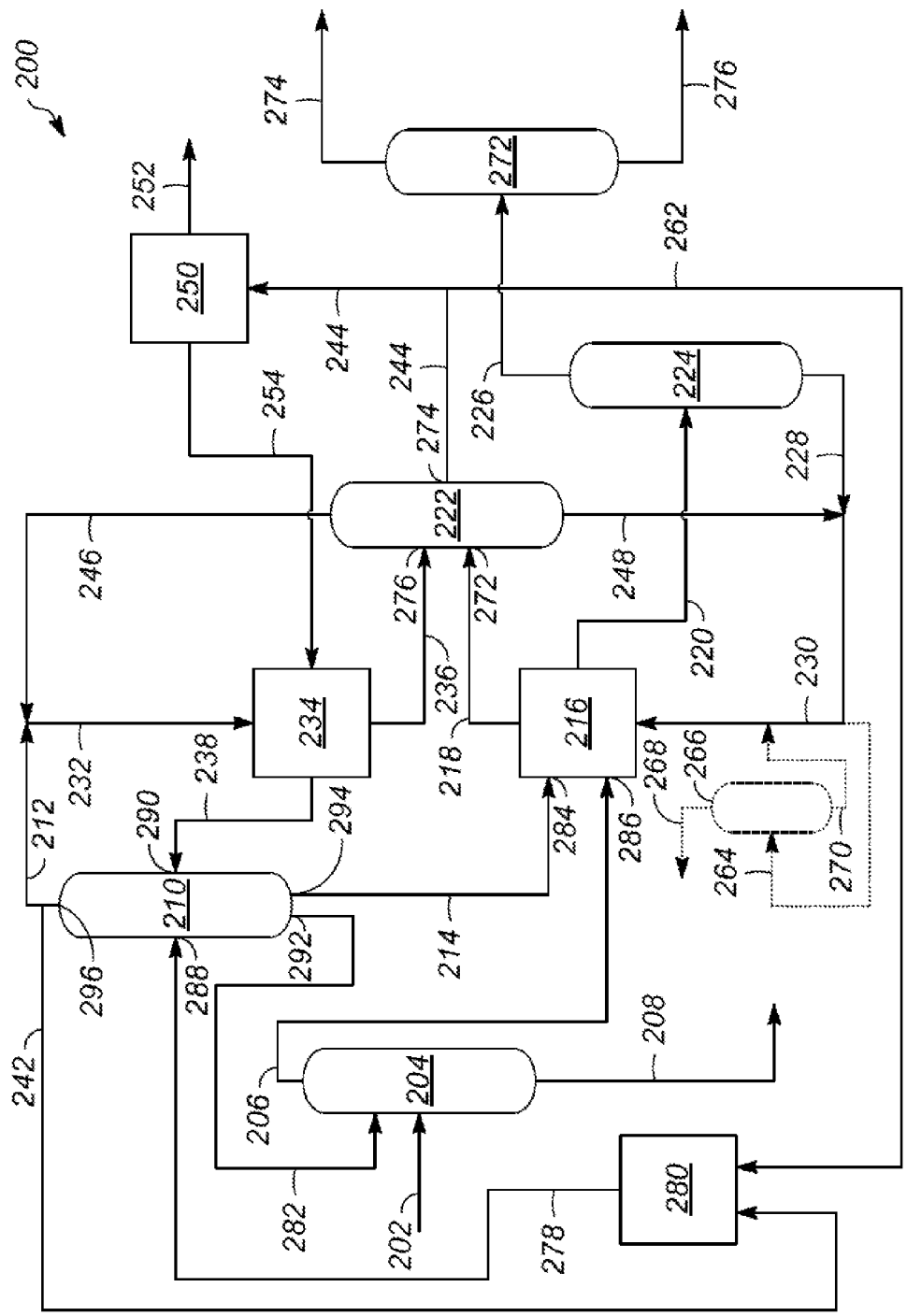
FIG. 2 is a diagram of an embodiment of a process for separating aromatic hydrocarbons employing a split-shell fractionation column as in FIG. 1.

The following example is merely provided to illustrate one possible implementation of a split-shell fractionation column in a broader aromatic hydrocarbon processing system. As such, the form and content of the various material streams are intended to serve only as a non-limiting example for the skilled artisan to better understand the operation thereof FIG. 2 illustrates an embodiment 200 of an aromatic hydrocarbon processing system that includes split-shell fractionation column 210, described above. A feed stream 202 enters a xylene fractionation unit 204. In one embodiment, the feed stream 202 contains ortho-, meta-, and para-xylene isomers. In one embodiment, the feed stream 202 contains quantities of ethylbenzene, toluene, $C_8$ cycloalkanes, alkanes, and hydrocarbons having more than eight carbon atoms per molecule. In one embodiment, the feed stream 202 is a result of hydrotreating naphtha to remove any sulfur and nitrogen contaminants and the subsequent catalytic reforming where paraffins and naphthenes in the decontaminated naphtha are converted to aromatic hydrocarbons. Most $C_7$— fractions are removed in a debutanizer and fractional distillation column, respectively.

The feed stream 202, including a $C_8$+ fraction, enters the xylene fractionation unit 204. In one embodiment, the feed stream 202 includes about 23 weight percent (wt %) para-xylene. The xylene fractionation unit 204 is a fractional distillation column. The xylene fractionation unit 204 divides the incoming stream into an overhead stream 206 including the $C_8$— aromatic hydrocarbons, including the xylene isomers, ethylbenzene, and toluene, a bottom product stream 208, and one or more side cut streams (not shown) including $C_9$+ aromatic hydrocarbons and any $C_7$— fractions present in the feed stream 202.

The overhead stream 206 from xylene fractionation unit 204, and a bottom product stream 214 from extract column 210, enter adsorptive separation unit 216 at a first feed input 286 and a second feed input 284, respectively. Adsorptive separation unit 216 separates the incoming streams 206 and 214 into a raffinate stream 218 and an extract stream 220. In one embodiment, the heavy desorbent para-diethylbenzene is used to facilitate the separation of the raffinate stream 218 and extract stream 220. The raffinate stream 218 includes ethylbenzene, meta-xylene, and ortho-xylene diluted with desorbent. The extract stream 220 includes para-xylene diluted with desorbent.

In one embodiment, adsorptive separation unit 216 includes a simulated moving bed (SMB) assembly and a rotary valve. The SMB assembly includes a single physical chamber. In one embodiment, the physical chamber includes 24 beds. In an alternative embodiment, the physical chamber includes less than 24 beds. In another embodiment, the SMB assembly includes two physical chambers. In one embodiment, each physical chamber includes 12 beds. In an alternative embodiment, each physical chamber includes more or less than 12 beds. In one embodiment, the physical chambers have an unequal number of beds. A bed line connects each bed in the SMB assembly to the rotary valve. The rotary valve controls the flow of material into or out of the SMB assembly in a step-wise manner to create a simulated moving bed and to flush the bed lines between flows of differing materials.

As a mixture of xylene isomers is fed into adsorptive separation unit 216, and flows downwardly under the force of gravity, the mixture of xylene isomers contacts a solid, zeolitic adsorbent within the chamber. The zeolitic adsorbent disposed in adsorptive separation unit 216 has an affinity for para-xylene. As the mixture of xylene isomers flows over the solid adsorbent, the para-xylene is selectively adsorbed into the adsorbent while the other isomers continue to travel downward in the chamber in the bulk liquid. In certain embodiments, the selectivity of the adsorbent in the adsorptive separation unit 216 for $C_7$— aromatic hydrocarbons and lighter hydrocarbons is very close to that of para-xylene. As such, the $C_7$— aromatic hydrocarbons and lighter hydrocarbons exit the adsorptive separation unit 216 by way of extract stream 220. The extract stream 220 enters the extract column 224. Extract column 224 is a fractional distillation column that separates the incoming stream 220 into an overhead para-xylene stream 226 including para-xylene, $C_7$— aromatic hydrocarbons, and lighter hydrocarbons and a bottom product stream 228 including a heavy desorbent fraction, such as para-diethylbenzene (a $C_{10}$ aromatic hydrocarbon). The bottom product stream 228 is recycled back to the adsorptive separation unit 216 through combined stream 230.

Light desorbent enters adsorptive separation unit 234 by way of combined stream 232. Adsorptive separation unit 234 separates an incoming stream 254 into a raffinate stream 236 and an extract stream 238. Stream 254 is an isomerized stream from isomerization unit 250 including an equilibrium mixture of xylene isomers. In one embodiment, the light desorbent toluene is used to facilitate the separation of the raffinate stream 236 and extract stream 238. The raffinate stream 236 includes ethylbenzene, meta-xylene, and ortho-xylene diluted with desorbent. The extract stream 238 includes para-xylene diluted with desorbent.

In one embodiment, adsorptive separation unit 234 includes an SMB assembly and a rotary valve. In one embodiment, the SMB assembly includes a single physical chamber. In one embodiment, the physical chamber includes 24 beds. In an alternative embodiment, the physical chamber includes less than 24 beds. In one embodiment, the SMB assembly includes two physical chambers. In one embodiment, each physical chamber includes 12 beds. In an alternative embodiment, each physical chamber includes more or less than 12 beds. In one embodiment, the physical chambers have an unequal number of beds. A bed line connects each bed in the SMB assembly to the rotary valve. The rotary valve controls the flow of material into or out of the SMB assembly in a stepwise manner to create a simulated moving bed and to flush the bed lines between flows of differing materials.

As a mixture of xylene isomers is fed into adsorptive separation unit 234, and flows downwardly under the force of gravity, the mixture of xylene isomers contacts a solid, zeolitic adsorbent within the chamber. The zeolitic adsorbent disposed in adsorptive separation unit 234 has an affinity for para-xylene. As the mixture of xylene isomers flows over the solid adsorbent, the para-xylene is selectively adsorbed into the adsorbent while the other isomers continue to travel downward in the chamber in the bulk liquid. The raffinate stream 236 enters a raffinate column 222 at a third location 276. The extract stream 238 and the output 278 from aromatic conversion unit 280 are fed into the split-shell extract column 210 (thereby become input streams 238, 278 to the column 210), which was described in greater detail above with regard to FIG. 1, at a first input port 290 and second input port 288, respectively. The split-shell column 210 separates the input streams into the previously described overhead stream 212 at third output 296 and the previously described bottom product streams 214 and 282 at first output port 294 and second output port 292, respectively. As previously noted, the overhead stream 212/242, in one embodiment, includes primarily toluene. In one embodiment, stream 212/242 includes also includes $C_7-$ aromatic hydrocarbons and lighter hydrocarbon impurities. The bottom product stream 214 includes $C_8$ aromatic hydrocarbon isomers, including a high concentration of para-xylene (as compared to stream 282). The bottom product stream 282 includes $C_8$ aromatic hydrocarbon isomers. In one embodiment, the bottom product stream 282 has a lower concentration of para-xylene than does bottom product stream 214. The light desorbent, in one embodiment toluene, is recycled in a light desorbent loop 212, 232, 238. In one embodiment, a slipstream 242 is extracted from the overhead stream 212/242. In one embodiment, slipstream 242 prevents the accumulation of additional toluene introduced into the desorbent loop from the feed stream 202. In one embodiment, slipstream 242 prevents the accumulation of light hydrocarbon impurities in the light desorbent loop. In one embodiment, slipstream 242 includes high purity toluene. In one embodiment, slipstream 242 includes toluene and light hydrocarbon impurities from the feed stream 202.

Raffinate column 222 is a fractional distillation column that separates the raffinate stream 236 and 218, each including para-xylene depleted $C_8$ aromatic hydrocarbon isomers diluted with light and heavy desorbent, respectively, into a $C_8$ aromatic hydrocarbon isomer stream 244, a light desorbent stream 246, and a heavy desorbent stream 248. The $C_8$ aromatic hydrocarbon isomer stream 244 exits the raffinate column 222 at a second location 274. The light desorbent along with any light impurities have the lowest boiling point and are, as such, extracted as a net overhead stream 246. The heavy desorbent along with any heavy hydrocarbons ($C_9+$) have the highest boiling point and are, as such, extracted as a net bottom product stream 248. The ortho-xylene, meta-xylene, and ethylbenzene have an intermediate boiling point and are, as such, extracted at a sidecut tray. The heavy desorbent is recycled in a heavy desorbent loop 230, 220/218, 228/248. In one embodiment, the $C_8$ aromatic isomer stream 244 exits the raffinate column 222 at a location below that of raffinate stream 236 and above that of raffinate stream 218. In one embodiment, the raffinate stream 236 enters raffinate column 222 at a location on the column where the composition within the column 222 is similar to the composition in stream 236. In one embodiment, the raffinate stream 218 enters raffinate column 222 at a location on the column where the composition within the column 222 is similar to the composition in stream 218.

The $C_8$ aromatic hydrocarbon isomer stream 244 including meta-xylene, ortho-xylene, and ethylbenzene enters an isomerization unit 250. Catalysts in the isomerization unit 250 reestablish an equilibrium mixture of the ortho-, meta-, and para-xylene isomers. In one embodiment, the catalyst is an ethylbenzene dealkylation catalyst, which converts ethylbenzene to a benzene co-product. In one embodiment, the catalyst is an ethylbenzene isomerization catalyst, which converts the ethylbenzene into additional xylene isomers. Non-aromatic compounds in the $C_8$ aromatic hydrocarbon isomers stream 244 are "cracked" (C—C bonds broken) to lighter hydrocarbons and removed in stream 252 along with any benzene co-product created. The isomerization process may also create small quantities of $C_9$ and heavier aromatic hydrocarbons. In one embodiment, the output stream 254 includes an equilibrium mixture of xylene isomers. In one embodiment, the output stream 254 includes small quantities of $C_9+$ aromatic hydrocarbons. In one embodiment, the output stream 254 includes unreacted ethylbenzene. In one embodiment, the output stream 254 includes about 1.5 wt. % ethylbenzene or less. The isomerized output stream 254 enters adsorptive separation unit 234.

In certain embodiments, some $C_9+$ aromatic hydrocarbons may be introduced as a result of the isomerization of ortho-xylene, meta-xylene, and ethylbenzene at isomerization unit 250. Any $C_{10}+$ hydrocarbons will accumulate in the heavy desorbent loop 230, 220/218, 228/248. In certain configurations of the raffinate column 222, any $C_9$ aromatic hydrocarbons will accumulate in the isomerization loop 254, 236, 244. In other configurations of the raffinate column 222, any $C_9$ aromatic hydrocarbons will accumulate in the heavy desorbent loop 230, 220/218, 228/248. In yet other configurations of the raffinate column 222, any $C_9$ aromatic hydrocarbons will accumulate in both the isomerization loop and the heavy desorbent loop. In different embodiments, one or more drag streams are used to prevent the accumulation of $C_9+$ aromatic hydrocarbons in the process. In one embodiment, if accumulation occurs in the heavy desorbent loop, a drag stream 264 is withdrawn from the desorbent loop by way of stream 230. Stream 230 includes primarily heavy desorbent along with the $C_9$ aromatic and heavier hydrocarbon impurities. The drag stream 264 is fed into a fractional distillation column 266, which separates the drag stream 264 into an overhead stream 268 and a bottom product stream 270. The bottom product stream 270 includes high purity para-diethylbenzene, which is returned to the desorbent loop by way of stream 230. In one embodiment, the amount of material withdrawn in drag stream 264 is about 1 to about 20 volume percent of stream 230. In another embodiment, if accumulation occurs in the isomerization loop (i.e., 254, 236, 244), a drag stream 262 is withdrawn from the isomerization loop by way of raffinate stream 244. Stream 262 includes a mixture of ortho-xylene, meta-xylene, ethylbenzene along with the $C_9$ aromatic and heavier hydrocarbon impurities. In one embodiment, the amount of material in the drag stream 262 is about 1 to about 20 volume percent of the raffinate stream 244. In yet another embodiment, if the accumulation occurs in both the isomerization loop and the heavy desorbent loop, drag streams 262 and 264 are both used. In other embodiments, no drag streams are used. In other embodiments, the impurities are extracted by another process known in the art capable of separating $C_9$ aromatic hydrocarbons and heavier hydrocarbons from para-diethylbenzene.

In one embodiment, the aromatic conversion unit 280 converts the incoming stream 262, including a mixture of toluene and $C_9+$ aromatic hydrocarbons, into an output stream 278 including an equilibrium mixture of xylene isomers, ethylbenzene, and toluene. The aromatic conversion unit 280 facilitates catalytic disproportionation reactions, which convert toluene into a mixture of benzene and xylene isomers. The aromatic conversion unit 280 also facilitates catalytic transalkylation reactions, which convert a blend of toluene and $C_9$ aromatic isomers to xylene isomers through the migration of methyl groups between methyl-substituted aromatic hydrocarbons. Benzene produced in the aromatic conversion assembly is extracted in an additional stream (not shown). The output stream 278 is fed into the split-shell extract column 210 of the present disclosure (described in greater detail above with regard to FIG. 1), which separates the output stream 278 into an overhead stream including toluene and a bottom product stream 282 including $C_8+$ aromatic hydrocarbons. The bottom product stream 282 is fed back into the xylene fractionation column 204 to separate the $C_8$ aromatic hydrocarbons into stream 206 and the $C_9+$ aromatic hydrocarbons into stream 208. The overhead toluene stream from the split extract column 210 is split into streams 212 and 242. Stream 242 is recycled back into the aromatic conversion unit 280 for transalkylation. Stream 212 is part of the light desorbent loop 212, 232, 238.

The finishing column 272 separates the overhead stream 226 from extract column 224 into an overhead stream 274 including $C_7-$ aromatic hydrocarbons and lighter hydrocarbons, and a bottom product stream 276 including high purity para-xylene. In certain embodiments, para-ethyltoluene, structurally similar to para-xylene, may be introduced into the process by the isomerization unit 250. In some embodiments, the para-ethyltoluene is separated from the para-xylene in the adsorptive separation unit 216, in the extract column 224, or in the finishing column 272. In some embodiments, the para-ethyltoluene is removed from the para-xylene product using techniques known in the art. In one embodiment, the bottom para-xylene stream 276 includes about 95.0 wt. % para-xylene. In one embodiment, the bottom para-xylene stream 276 includes about 99.2 wt. % para-xylene. In one embodiment, the bottom para-xylene stream 276 includes about 99.7 wt. % para-xylene. In one embodiment, the bottom para-xylene stream 276 includes about 99.9 wt. % para-xylene. In one embodiment, the bottom para-xylene stream 276 includes greater than about 99.9 wt. % para-xylene.

Accordingly, an improved split-shell fractionation column has been described. The improved column beneficially mitigates the risk of leakage and cross-contamination of liquid bottom products at the bottom of the split-shell fractionation column. Furthermore, the improved column desirably reduces capital and energy costs by combining two fractionation columns into a single column that has a common overhead distillate product but dissimilar liquid bottom products.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the processes without departing from the scope defined by the claims, which includes known equivalents and foreseeable equivalents at the time of this disclosure.

What is claimed is:

1. A split-shell fractionation column comprising:
a housing shell having a first height;
a partition having a second height and disposed within the housing shell, wherein the partition comprises:
first and second vertically oriented baffles separated by a gap region;
a seal plate connecting top ends of the baffles;
a first input port formed to extend through the partition for the introduction of a gas into the gap region; and
a first output port formed to extend outwardly from a bottom of the gap region and through the housing shell,
wherein the partition defines a first distillation zone and a second distillation zone within the housing shell and wherein the gap region is configured to be operated at a pressure different than a pressure within the housing shell.

2. The split-shell fractionation column of claim 1, further comprising a second input port formed to extend through the housing shell and open into the first distillation zone.

3. The split-shell fractionation column of claim 2, wherein the second input port is provided at a height along the housing shell that is lower that the height of the partition.

4. The split-shell fractionation column of claim 2, further comprising a second output port formed to extend outwardly from the first distillation zone and through the housing shell.

5. The split-shell fractionation column of claim 4, further comprising a third input port formed to extend through the housing shell and open into the second distillation zone.

6. The split-shell fractionation column of claim 5, wherein the third input port is provided at a height along the housing shell that is lower that the height of the partition.

7. The split-shell fractionation column of claim 5 further comprising a third output port formed to extend outwardly from the second distillation zone and through the housing shell.

8. The split-shell fractionation column of claim 7, further comprising a fourth output port formed to extend outwardly from an overhead region of the column and through the housing shell.

9. The split-shell fractionation column of claim 1, wherein the first distillation zone comprises a first plurality of distillation trays and wherein the second distillation zone comprises a second plurality of distillation trays.

10. The split-shell fractionation column of claim 9, wherein the first distillation zone has a greater number of distillation trays than the second distillation zone.

11. The split-shell fractionation column of claim 1, wherein the gas in the gap region comprises nitrogen or an inert gas.

12. The split-shell fractionation column of claim 1, wherein the first and second vertically oriented baffles are welded to the housing shell.

13. The split-shell fractionation column of claim 1, wherein the pressure of the gap region is lower than the pressure within the housing shell.

14. The split-shell fractionation column of claim 1, wherein the gap region has a width between the first and second baffles from about 25 mm to about 50 mm.

15. The split-shell fractionation column of claim 1, wherein the partition prevents fluid at a bottom of the first fractionation zone from flowing into a bottom of the second fractionation zone.

16. The split-shell fractionation column of claim 1, wherein the partition is configured to collect leakage liquid bottom product from the first fractionation zone and leakage liquid bottom product from the second fractionation zone.

* * * * *